(12) United States Patent
Troup

(10) Patent No.: US 7,856,323 B2
(45) Date of Patent: Dec. 21, 2010

(54) METHOD FOR ANALYZING BLOOD FOR LIPOPROTEIN COMPONENTS

(75) Inventor: Jan M. Troup, The Woodlands, TX (US)

(73) Assignee: Spectracell Laboratories, Inc., Houston, TX (US)

( * ) Notice: Subject to any disclaimer, the term of this patent is extended or adjusted under 35 U.S.C. 154(b) by 173 days.

(21) Appl. No.: 11/611,497

(22) Filed: Dec. 15, 2006

(65) Prior Publication Data

US 2008/0038763 A1    Feb. 14, 2008

Related U.S. Application Data

(63) Continuation-in-part of application No. 11/464,044, filed on Aug. 11, 2006, now abandoned.

(51) Int. Cl.
  *G01N 33/48* (2006.01)
(52) U.S. Cl. ........................................ 702/19
(58) Field of Classification Search ............ 702/19
  See application file for complete search history.

(56) References Cited

U.S. PATENT DOCUMENTS

| | | | |
|---|---|---|---|
| 6,010,866 A | 1/2000 | Ollington et al. |
| 6,593,145 B2 | 7/2003 | Macfarlane et al. |
| 6,753,185 B2 | 6/2004 | Macfarlane et al. |
| 6,808,889 B2 | 10/2004 | Fitzpatrick et al. |
| 2006/0014299 A1 | 1/2006 | Troup |

OTHER PUBLICATIONS

Gross et al., "Molecular Counting of Low-Density Lipoprotein Particles as Individuals and Small Clusters on Cell Surfaces," Biophysical Journal (1986) pp. 901-911.*

Chapman et al., "A Density Gradient Ultracentrifugal Procedure for the Isolation of the Major Lipoprotein Classes from Human Serum," Journal of Lipid Research (1981) vol. 22, pp. 339-358.*

Dergunov et al., "Charge-based Heterogeneity of Human Plasma Lipoproteins at Hypertriglyceridemia: Capillary Isotachophoresis Study," The International Journal of Biochemistry and Cell Biology (2003) vol. 35, pp. 530-543.*

Chandra et al., "Remnant lipoprotein density profiling by CsBiEDTA density gradient ultracentrifugation", Anal Chem.; 2006; 680-5; vol. 78(3).

Espinosa et al., "Method for Lipoprotein(a) Density Profiling by BiEDTA Differential Density Lipoprotein Ultracentrifugation", *Anal. Chem.*; 2006; 438-444, vol. 78 (2).

Johnson et al., "Metal Ion Complexes of EDTA as Solutes for Density Gradient Ultracentrifugation: Influence of Metal Ions", *Anal. Chem.*; 2005; 7054-7061, vol. 77(21).

Hosken et al., "Metal ion complexes of EDTA: a solute system for density gradient ultracentrifugation analysis of lipoproteins", Anal Chem.; 2005; 200-207; vol. 77(1).

Kwiterovich et al., "A large high-density lipoprotein enriched in apolipoprotein C-I: a novel biochemical marker in infants of lower birth weight and younger gestational age", JAMA, 2005; 1891-1899; vol. 293(15).

Liu et al., "Charge density profiling of circulating human low-density lipoprotein particles by capillary zone electrophoresis", Electrophoresis, vol. 25(17), 2985-2995, Sep. 2004.

International Search Report issued Sep. 10, 2008 during the prosecution of International Application No. PCT/US2007/075445.

Written Opinion issued Sep. 10, 2008 during the prosecution of International Application No. PCT/US2007/075445.

International Preliminary Report on Patentability issued Feb. 17, 2009 (Published Feb. 17, 2009), during the prosecution of International Application No. PCT/US2007/075445.

* cited by examiner

*Primary Examiner*—Jerry Lin
(74) *Attorney, Agent, or Firm*—Fulbright & Jaworski, L.L.P.

(57) ABSTRACT

A new lipoprotein analysis procedure based on the CDC gold standard, analytical ultra centrifugation, having dramatically reduced the time and cost to obtain a result with a self generating continuous gradient. The method allows quantification of the risk factors of cardiovascular disease based on particle numbers of the particles of various groups and subgroups of lipoproteins.

28 Claims, 1 Drawing Sheet

METHOD FOR ANALYZING BLOOD FOR LIPOPROTEIN COMPONENTS

CROSS-REFERENCE TO RELATED APPLICATIONS

This application is a continuation-in-part of, and claims priority to, application Ser. No. 11/464,044, filed Aug. 11, 2006.

TECHNICAL FIELD

The present invention relates to a method and apparatus for analyzing lipoprotein components in blood of an animal including a human.

More particularly, the present invention relates to a method and apparatus for analyzing lipoprotein components in blood of an animal including a human, where the method includes the step of mixing a serum sample with a fluorescent dye and a self generating gradient material, developing an analyzable mixture in a centrifuge tube under increased gravity via application of external centrifugal force and analyzing the resulting developed mixture to generate a detailed lipoprotein particle component analysis.

BACKGROUND OF THE INVENTION

Human blood serum contains lipoproteins whose values are traditionally determined by a lipid panel and used by physicians to diagnosis and treat patients for cardiovascular disease.

The National Cholesterol Education Program (NCEP) acknowledges that 50% of the people with cardiovascular disease are missed by the standard lipid panel tests for total cholesterol, triglycerides, high density lipoprotein (HDL) and calculated low density lipoprotein (LDL). NCEP described in the latest ATP III (Adult Treatment Program III) guidelines, new emerging risk factors that are important in the diagnosis and treatment of those people missed by the standard lipid panel. NCEP does not generally recommend analysis of the new emerging risk factors due to the lack of availability and the cost of these tests. None the less a number of companies have emerged to address this need and supply information on these risk factors.

Lipoproteins are spherical particles composed of hundreds to thousands of molecules. Each particle has at least one apolipoprotein which distinguishes it as a VLDL, LDL, or HDL particle. VLDL and LDL particles have one molecule of apolipoprotein B and HDL molecules have one or more molecules of apolipoprotein A on the surface of the particle. In addition, the surface of the particle is covered with phospholipids and unesterified cholesterol. The interior of lipoproteins is composed of cholesterol ester and triglycerides with most of the triglycerides being found in the VLDL lipoprotein.

In the Standard Lipid Panel, LDL is calculated (not directly measured) from assumptions about the cholesterol content of very low density lipoprotein (VLDL) knowing the triglyceride values and directly measured total cholesterol and HDL. This result can have a 20% or larger LDL cholesterol error as determined in studies and even greater error when compared to lipoprotein particle numbers. LDL measured directly for cholesterol content is a somewhat better measurement. However, high or very low triglycerides and other substances can interfere, precluding accurate results. The cholesterol, as a surrogate marker, is assumed to correlate with LDL particle numbers. This is not the case for many individuals, giving up to a 30% or greater error when compared to particle number values.

A number of methods have been developed as cost and time saving alternatives to the CDC method of cholesterol analysis to provide information on the new lipoprotein emerging risk factors as identified in the NCEP guidelines for the diagnosis and treatment of people at risk of cardiovascular disease. Historically, the CDC method using gradient separation of the lipoproteins in the blood by analytical ultracentrifugation is know as the gold standard in identifying the lipoprotein classes of VLDL, LDL and HDL. The CDC method, however does not break down lipoproteins into subgroups which are necessary for the identification of the new emerging risk factors. To extend the CDC method with sequential multiple gradient separations of subgroups is very time consuming and expensive. In view of these problems other methods have been developed to give information that approximates an extended CDC sequential separation with techniques that are faster and/or less costly than the CDC method.

Thus, there is considerable room for improvement in the development of a new test which more accurately indicates risk of cardiovascular disease (CVD).

BRIEF SUMMARY OF THE INVENTION

The present invention is directed to a diagnostic method in which all lipoprotein are measured directly for the number of lipoprotein particles. The method results in an accurate test that does not make assumptions regarding other lipoproteins or the cholesterol content of the LDL or other lipoproteins. The LDL particle number result, either expressed as the cholesterol equivalent or directly as a number is the most clinically relevant result on which to base lifestyle changes or drug therapy.

In one aspect of the present invention, there is method of evaluating the lipoprotein profile of a non-human animal or human, said method comprising: (a) obtaining a blood sample of said non-human animal or human; (b) separating serum from said blood sample; (c) delivering the serum to a centrifuge tube and adding an analyte material and a self generating gradient material to form a mixture; (d) centrifuging some or all of the mixture; (e) extracting the centrifuged mixture to form an extracted mixture; (f) measuring an analytical signal from the extracted material; (g) recording data comprising said analytical signal; (h) converting said data to cholesterol equivalent data, said step of converting comprising the step of transforming the data with a SAVR function for each lipoprotein group and/or subgroup, wherein said data is normalized with said function for the potential cholesterol content contained within each particle; (i) transforming said cholesterol equivalent data using a calibration process with data from lipoprotein cholesterol; and, (j) thereafter calculating particle number data from said transformed cholesterol equivalent data. In preferred embodiments, the step of transforming said cholesterol equivalent data using a calibration process with data from lipoprotein cholesterol standards comprises the use of data from lipoprotein cholesterol standards that neither have a high probability of being cholesterol enriched nor have a high probability of being cholesterol depleted; and, that are neither predominantly buoyant nor predominantly dense. In preferred embodiments, the step of measuring an analytical signal comprises passing the extracted mixture through a flow cell. In preferred embodiments, further comprising the step of incubating at an elevated temperature after step (c). In preferred embodiments, the step of incubation at an elevated temperature comprises incubating at 23-50° C. The method of claim 4, wherein said step of incubating further comprises vortexing the mixture. In preferred embodiments, the step of adding a self generating gradient material comprises delivering a composition comprising a compound selected from the group consisting of Nycodenz, Iodixanol, and any combination thereof. In preferred embodiments, the step of adding an analyte material comprises adding a fluorescent dye. In preferred embodiments, the step of measuring an analytical signal comprises measuring fluorescence. In preferred embodiments wherein a fluorescent dye is added as an analyte material, the step of adding a fluorescent dye comprises adding NBD C6-ceramide dye. In some embodiments, the step of adding an analyte material comprises adding an environment-sensitive chromophore. In some embodiments using a chromophore, the step of measuring an analytical signal comprises measuring absorbance. In some embodiments, the step of adding an analyte material comprises adding a radio isotope. In some embodiments using a radio isotope, the step of measuring an analytical signal comprises measuring radiation emitted by said radio isotope. In some embodiments, the step of centrifuging comprises centrifuging at about 120,000 rpm and about 7° C. for about 4.0 hours. Preferably, the method further comprises the step of adding a dilute phosphate buffer and centrifuging for about 30 minutes at about 120,000 rpm at about 7° C., said step of adding dilute phosphate buffer and centrifuging for about 30 minutes being performed after said step of centrifuging at about 120,000 rpm and about 7° C. for about 4.0 hours. Preferably, the step of adding a dilute phosphate buffer comprises adding about 10-300 μL of said dilute phosphate buffer. Preferably, the step of centrifuging comprises centrifuging at about 120,000 rpm and about 22° C. for about 3.0 hours. Preferably, the method further comprises the step of adding a dilute phosphate buffer and centrifuging for about 30 minutes at about 120,000 rpm at about 22° C., said step of adding dilute phosphate buffer and centrifuging for about 30 minutes being performed after said step of centrifuging at about 120,000 rpm and about 22° C. for about 3.0 hours. In preferred embodiments, the step of extracting comprises separating fractions of different densities of said mixture. In preferred embodiments, the step of passing the extracted mixture through a flow cell comprises pumping said extracted mixture with an HPLC pump. In preferred embodiments, the method further comprises the step of correcting said data for start position and using a time scale converted to a density scale, said density scale determined by collecting fractions from said step of extracting. In the embodiments wherein the data is corrected for start position and a time scale is used to convert to a density scale, the step of converting said data to cholesterol equivalent data preferably further comprises the step of making small empirical adjustments to said function using known cholesterol standards to account for the differences in the phospholipids shell of each lipoprotein type and dye uptake. In preferred embodiments, the step of correlating comprises calculating a lipoprotein particle number or a cholesterol equivalent value from said data. In preferred embodiments, the step of delivering the serum to a centrifuge tube comprises delivering about 1-30 μL to said centrifuge tube. In preferred embodiments, the step of adding an analyte material and a self generating gradient material comprises adding about 100-1500 μL of said self generating gradient material. Preferably, the step of adding an analyte material comprises adding about 1-30 μL of a dye solution. In preferred embodiments, the step of delivering the serum to a centrifuge tube and adding an analyte material and a self generating gradient material to form a mixture comprises delivering a total volume of 100-1200 μL.

In another aspect of the present invention, there is a method of evaluating the lipoprotein profile of a non-human animal or human, said method comprising: separating a serum sample from said non-human animal or human into fractions, said fractions enriched in lipoproteins of densities within a range of densities; detecting an analytical signal from said fractions; normalizing the analytical signal with a function which correlates the magnitude of the analytical signal with a lipoprotein particle number; and, calculating the number of particles corresponding to said fractions. In preferred embodiments, the step of detecting an analytical signal comprising detecting fluorescence from a fluorophore bound to said lipoproteins. In some embodiments wherein a step of detecting fluorescence from a fluorophore bound to said lipoproteins, the fluorophore is preferably NBD C6-ceramide. Preferably, the step of separating a serum sample from said animal or human into fractions comprises introducing said sample into a self generating gradient material and centrifuging the resulting mixture. In preferred embodiments, the step of detecting an analytical signal comprising detecting scattered light from one or more of said fractions enriched in lipoproteins of densities within a range of densities.

In another aspect of the present invention, there is a method of evaluating the lipoprotein profile of a non-human animal or human, said method comprising: (a) obtaining a blood sample of said non-human animal or human; (b) separating serum from said blood sample; (c) delivering the serum to a centrifuge tube and adding an analyte material and a self generating gradient material to form a mixture; (d) centrifuging some or all of the mixture; (e) extracting the centrifuged mixture to form an extracted mixture; (f) measuring an analytical signal from the extracted material; (g) recording data comprising said analytical signal; (h) transforming said data comprising said analytical signal by dividing by a SAVR function; (i) fitting said data to a mathematical function; (j) integrating said fitted data at defined lipoprotein subgroup densities to determine values on a cholesterol scale; (k) scaling the fitted and integrated data using known cholesterol standards; and, (l) using said scaled data to calculate lipoprotein particle numbers. In preferred embodiments, the step of fitting said data to a mathematical function comprises fitting to a Gaussian function. In preferred embodiments, the step of scaling the fitted and integrated data using known cholesterol standards comprises scaling with known cholesterol standards that neither have a high probability of being cholesterol enriched nor have a high probability of being cholesterol depleted; and that are neither predominantly buoyant nor predominantly dense.

The foregoing has outlined rather broadly the features and technical advantages of the present invention in order that the detailed description of the invention that follows may be better understood. Additional features and advantages of the invention will be described hereinafter which form the subject of the claims of the invention. It should be appreciated by those skilled in the art that the conception and specific embodiment disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims. The novel features which are believed to be characteristic of the invention, both as to its organization and method of operation, together with further objects and advantages will be better understood from the following description when considered in connection with the accompanying figures. It is to be expressly understood, however, that each of the figures is provided for the purpose of illustration and description only and is not intended as a definition of the limits of the present invention.

BRIEF DESCRIPTION OF THE DRAWING

For a more complete understanding of the present invention, reference is now made to the following descriptions taken in conjunction with the accompanying drawing, in which.

DETAILED DESCRIPTION OF THE INVENTION

Figure 1:
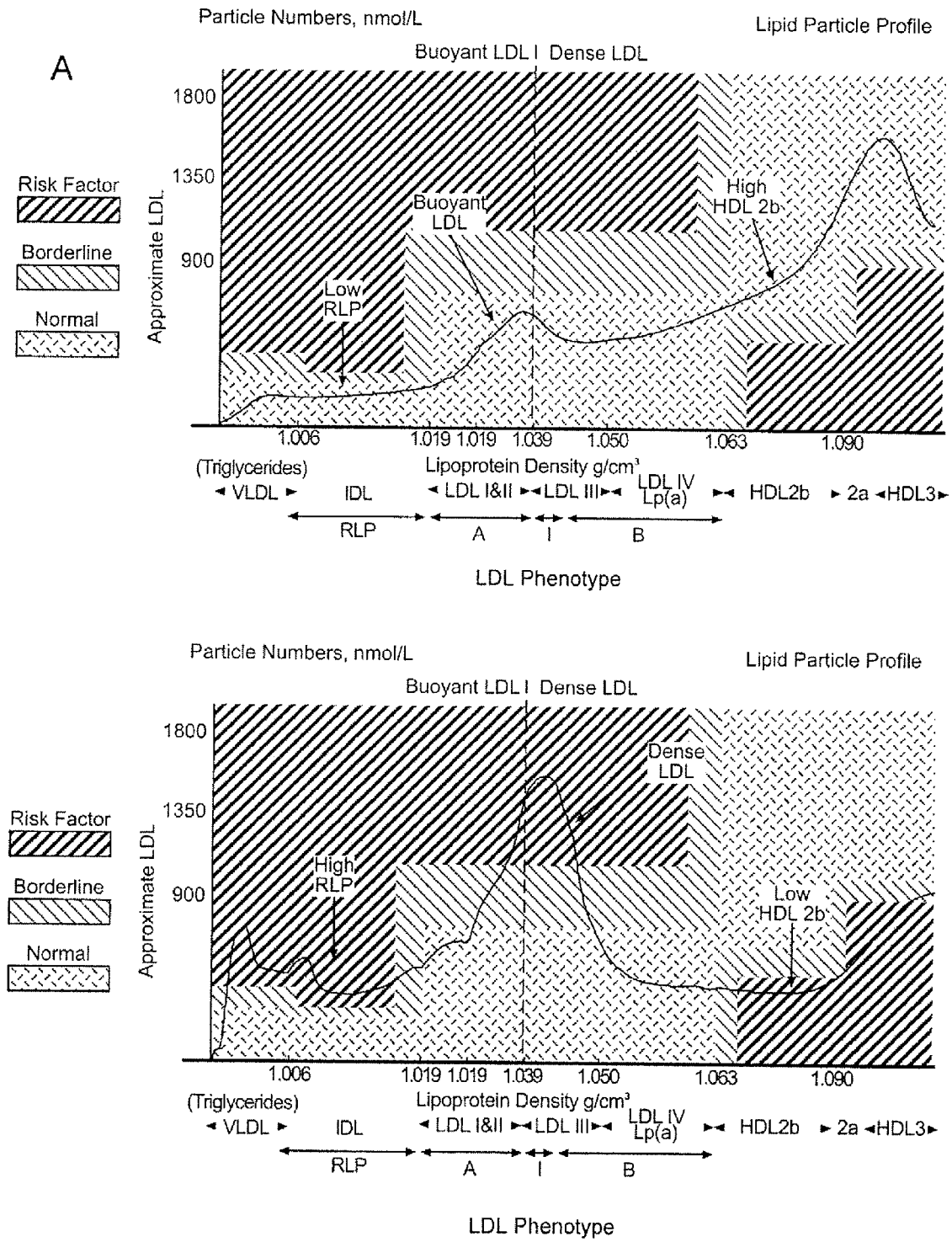
FIG. 1 illustrates (a) a healthy lipid number profile; and (b) an atherogenic profile.

As used herein, "cholesterol enriched" in reference to lipoproteins means lipoprotein particles that have a higher cholesterol content than the population average for a specific subgroup. "High probability of being cholesterol enriched" with respect to lipoprotein samples means having triglyceride values less than 75 mg/dL.

As used herein, "cholesterol depleted" in reference to lipoproteins means lipoprotein particle that have a lower cholesterol content than the population average for a specific subgroup. "High probability of being cholesterol depleted" with respect to lipoprotein samples means triglyceride values greater than 125 mg/dL.

As used herein, "buoyant" in reference to lipoproteins means lipoprotein particles that are predominately larger or more buoyant that the average population. "Predominantly buoyant" with respect to lipoprotein samples means mean density value less than 1.028 $g/cm^2$ for LDL and less than 1.085 $g/cm^2$ for HDL.

As used herein, "dense" in reference to lipoproteins means lipoprotein particles that are predominately smaller or more dense that the average population. "Predominantly dense" means with respect to lipoprotein samples means mean density value greater than 1.032 $g/cm^2$ for LDL and less than 1.100 $g/cm^2$ for HDL.

As used herein with respect to the mathematical treatment of data, a "transformation" (or the step of "transforming" data) means the application of a mathematical operator to a data set to create a second data set, wherein the original data set has elements related by the mathematical operator to elements in the second data set and vice versa.

The inventors have found that a new lipoprotein analysis procedure based on the CDC gold standard, analytical ultracentrifugation, having dramatically reduced the time and cost to obtain a result with a self generating continuous gradient, can be constructed and successfully implemented. The procedure can be used to ascertain the risk of CVD in a human or animal, but preferably is applied to a human. The advantage of this new technology is that all of the lipoproteins can be separated in a single spin in a number of hours rather than days required by the extended CDC method. Furthermore, the continuous gradient profile can be divided into slices by density to give accurate concentration reading of all lipoprotein subgroups at their specific densities. This lipoprotein subgroup information is the component needed to produce accurate information and data on all of the emerging new lipoprotein risk factors identified by the NCEP. This allows the present procedure to use the CDC gold standard, analytical ultracentrifugation separation technology rather than an approximation technology while allowing the technology to be extended to encompass determination of newly identified lipoprotein subgroups rendering accurate lipoprotein subgroup information.

The method of this invention includes a number of steps. Firstly, a blood sample must be procured. This can be done any way known to those of ordinary skill in the art, including collecting a blood sample via a venous draw into red top tubes with no anticoagulant or via a finger stick technology using an EDTA or other suitable anticoagulant. Serum is then separated from the blood sample and the serum is mixed, preferably with a fluorescent dye (although another analyte material may be used) and a self generating gradient material to form an analyzable mixture. A serum sample, preferably between 1 and 100 µL, is used. More preferably, the volume of the serum sample is in the range of 1-30 µL, most preferably, about 6.5 µL are used. Preferably, about 100-1500 µL of the gradient are used, more preferable 500-1000 µL are used, most preferably about 712 µL are used. The fluorophore is preferably NBD C6-ceramide at a concentration of 2 mg/mL in DMSO. When this solution is used, it is preferred to use about 1-30 µL of the dye solution, more preferably about 1-10 µL are used, most preferably, about 5 µL are used.

Optionally, the mixture is incubated at a temperature and for a time sufficient to facilitate uptake of the dye or other analyte. The incubation temperature is preferably about 23-50° C., more preferably about 30-40° C.; and most preferably about 37° C. The mixture is centrifuged (i.e., spun) at a preferred temperature of between about 20° C. and about 25° C.; a temperature about 22° C. being particularly preferred. A preferred spin rate is 120,000 rpm (revolutions per minute), although other rates may be used. Alternatively, the mixture is centrifuged at a temperature of between 4° C. and 10° C., preferably at 7° C. Preferably, about 100-1200 µL of solution is added to the centrifuge tube; more preferably, about 200-700 µL are added to the centrifuge tube; most preferably about 500 µL are added to the centrifuge tube. Preferably, the centrifuge time is 3.0 to 4.0 hours, although other centrifuge times are useful as well. The time and speed of the spin are interdependent. For example, a long spin time of about 12 to about 24 hours, with 17 hours being a preferred spin time, at a spin rate between about 80,000 and about 90,000 rpm, with a spin rate of about 85,000 rpm being preferred (about 250,000 g's) can be used. Also, a shorter spin time of about 3 to about 7 hours at a spin rate of about 120,000 rpm (over 600,000 g's) produces a similar result (with a spin time of about 3 hours being preferred). About thirty minutes or more before the end of the spin, the rotor is stopped and a layer of water or weak buffer between about 20 to 25° C. and preferably 22° C. is added on top of the mixture for the separation of IDL and VLDL subgroups; after the spinning step, the sample is stored in a substantially vertical orientation for a period of time less than about two hours at a temperature between about 20° C. and about 25° C. Preferably, about 10-300 µL of layering solution are used; more preferably about 50-150 µL are used; most preferably about 90 µL are used. Shortly, preferably immediately, after the storing step, the contents of the centrifuge tube is extracted with a plunger device having a hole in a center of the plunger (a plunger device available from Brandel is suitable, although others may be used). Any other device, known to those of ordinary skill in the art, which would deliver the contents of the centrifuge tube without substantial mixing of the segregated components is also applicable. In the preferred embodiment, the contents of the plunger are delivered into a fluorescence detector except for the last amount which is pushed out of the transfer tubing with an HPLC pump. The detector is calibrated and, in the case of use of a fluorophore as the analyte, its setting adjusted to emission and/or absorbance wavelengths of the dye. As the preferred embodiment is a flow technique, the method further includes correcting the resulting digital profile data for start position and first signal.

Fluorescent labeling of lipoproteins typically involves binding of fluorophores to the surface of the lipoprotein particle. In the case of the use of a fluorescent analyte which fluoresces only when associated with a lipoprotein particle, correction must be made for the varying capacities of different lipoprotein surfaces to incorporate fluorescent analyte molecules. Thus, when using fluorescence analytes, the data is preferably normalized with a correction routine that accounts for the differential incorporation of analyte by the various lipoprotein populations. Additionally, because the data is preferably presented on a cholesterol equivalent scale (a scale familiar to doctors and other health care professional), account must be made of the varying abilities of different types of lipoproteins to incorporate cholesterol. In the case of detection based on fluorescent label incorporation, the data is preferably corrected with a SAVR (surface area to volume ratio weighted by cholesterol content expressed as a fraction) correction routine, based on the theory that the surface dying of the lipoprotein particles is controlled by the size/volume relationship of the particles. For a given lipoprotein group or subgroup, the SAVR function is:

$$\left( \frac{\text{Surface Area}}{\text{Volume} \cdot \text{Cholesterol Content}} \right)$$

The cholesterol content term in the above equation is expressed as a fraction (i.e., 100% would correspond to a Cholesterol Content of 1). The corrected and normalized data is then converted from a time scale to a pre-calibrated density scale. The corrected and normalized density scale data is fitted with about 20 Gaussian functions at specific densities to get integrated data on a cholesterol mg/dl scale for the various lipoprotein subgroups. The data is correlated to the number of particles of one or more lipoprotein groups and/or subgroups. The profile of cholesterol (or lipoprotein subgroup particle number) versus density and the subgroup concentration and density data is preferably transferred to a spread sheet program to produce the final report.

Alternatively, the tube could be photographed as a measure of the fluorescence or alternatively a tuned light source and a wavelength selectable proximity detector could be used to detect the fluorescence. However, the preferred method of detector is the direct measurement of the steady state fluorescence emission.

Also, other analytical detection methods may be used. These include both spectroscopic and non-spectroscopic methods. For example, optical absorbance can be used. In this case, a chromophore is introduced in the same way that the use of a fluorophore was described above. An absorbance detector can also be used alone or in conjunction with the fluorescence detector to examine other features or markers of the separated sample not detected by fluorescence. The separated sample can be collected in a fraction collector for post separation analysis by other methods, if necessary. In addition the sample can be eluted through an HPLC separation column using size exclusion or other packing prior to going into the fluorescence detector to further separate the lipoprotein subgroups. Alternatively a radio label may be used. The detection scheme may use light scattering as a particle counting method. Scattering techniques such as Rayleigh, Raman, or Mie scattering may be used. Scattering techniques may measure scatter from a reporter (i.e., added) species similar to the fluorescence or absorbance schemes outlined above, or they may measure scatter directly from the lipoprotein particles.

In any scheme utilizing an added analyte as a reported species, it is preferable to correct the data for differential incorporation of analyte into the various lipoprotein particle populations. This is preferred both where the results are to be expressed on a cholesterol scale and where they are expressed in absolute particle numbers only. The SAVR function is one example of such a correction function where a particle counting detector can also be used. Because the different lipoprotein fractions are eluting through the detector at different times owing to their earlier separation, particle counting techniques can be used to determine the number of particles in each lipoprotein group and/or subgroup.

A venous draw is the preferred method of collecting a blood sample. However, finger stick technology may also be used. Finger stick technology must be done carefully to avoid modifying the lipoproteins. If a sample is obtained by medium to heavy messaging of the finger to get enough blood the HDL peak in the profile becomes much more buoyant and moves out of the theoretical range for HDL, less than 1.063 g/cm$^3$. Because HDL is a scavenger of lipids and since proteins are heavier than HDL and would not be found at a density greater than 1.20 g/cm$^3$, it is possible that the HDL may pick up free lipids generated by the aggressive activity. Thus the blood collection should only be done when the blood is freely flowing with minimal pressure applied to the finger to obtain the sample. The shift of the HDL is also seen when hemolysis is present in the sample and can be caused by not using an anti-coagulant. If a clot activator tube is used this causes hemolysis and an HDL shift. The use of heparin treated collection tubes or capillaries will cause the VLDL and some of the LDL to de-lipidate. This effect is clearly seen as a major reduction in the VLDL and LDL peaks and an increase in the protein peak. The only anti-coagulant that has been found to provide good profiles is EDTA, either as treated collection tubes or capillaries.

This process of the present invention preserves the sample, and fractions or subgroups can be collected in a fraction collector. The process involves removing the contents from the tube in way that will allow an HPLC pump to pump the contents through a size exclusion or other separation column for further separation of the lipoprotein subgroups and then on to the fluorescence detector and sample collector. Additional separation by HPLC should be applicable, followed by measurement without destruction of the lipoproteins.

It is preferable that the following experimental variables, incubation of the sample mixture, the temperature of the spin, holding the samples after the spin, the speed of sample extraction, the use of a small centrifuge tube, be precisely controlled to give rise to a better result.

The prior art gradient Na Bi EDTA separates the VLDL, LDL, HDL very well but the gradient starts at a density of about 1.020 g/cm$^3$. This means that all of the VLDL subgroups and IDL which make up the important emerging new risk factor RLP (remnant lipoprotein) are at the top of the tube and not separated. A solution to this problem involves adding a water or buffer layer on top of the tube (90 μL on top of 500 μL of gradient) during the last one half hour of the spin. The water slowly diffuses into the gradient and the lipoproteins find their proper density between 1.000 and 1.020 and are clearly separated. Others have used the addition of a layer of different density for separation but it has not been reported that a continuous gradient has been formed from 1.000 to 1.3+ g/cm³. It is believed that reaching a low density at the same time generating a density of 1.3 g/cm³ has not been done before.

A more preferred gradient may be formed using a triiodobenzene compound; the preferred commercially available example of which is the non-ionic mixture of Nycodenz and Iodixanol. Other gradients, known to those of ordinary skill in the art, may be substituted. Non-ionic gradient mixtures, such as the non-ionic mixture of Nycodenz and Iodixanol are preferred in the present invention, although mixtures of ionic components may be suitable in some cases. Nycodenz is 5-(N-2,3-dihydropropylacetamido)-2,4,6-triiodo-N,N'-bis (2,3-dihydropropyl)isophthalamide). Iodixanol is 5-5'-[2-hydroxy-1,3-propanediyl)-bis-(acetylamino)] bis [N,N'-bis(2,3-dihydroxypropyl-2,4,6,-triiodo-1,3-benzenecarboxamide]. In one embodiment, aqueous solutions of each component including 5.714 ml of Iodixanol, 40.00 ml of Nycodenz, preferably at 60% (w/v) and 125.34 ml water are combined to form the final gradient material. Salts tend to dehydrate lipoproteins to various degrees. Dehydration changes the density, and density is the basis for the ensuing separation. Thus, if excessive dehydration and concomitant density modification occurs, results may be acceptable, but may be less than ideal. One example of an ionic gradient material which is suitable in the present invention is Cs—Bi-EDTA complex.

Since the magnitude of the fluorescence of the dye varies depending on the lipoproteins and subgroup, and the separated lipoproteins are preferably on a common cholesterol scale, an algorithm was developed based on the theory that the surface dying of the particles is controlled by the surface area/volume relationship of the particles. The algorithm called SAVR for surface area volume ratio, the volume being weighted for cholesterol content, is empirically determined but the initial values were very close to the calculated values of the surface area to volume ratio, weighted for cholesterol content, from known measured data. Another factor that controls the dye uptake is the amount of phospholipids on the surface of the lipoprotein particles. The surface amount of phospholipids is not well known by subgroups. Although other fluorophores may be used, preferably, the fluorophore is an NBD dye, and the preferred NBD fluorescent dye is NBD C6 ceramide (6-((N-(7-nitrobenz-2-oxa-1,3-diazol-4-yl) amino)hexanoyl)sphingosine). It is a phospholipid analog and attaches to the surface of the lipoprotein particle as do phospholipids. Therefore the correction (for example, the SAVR function) being applied to the raw data is empirically adjusted to fit the known cholesterol values from a standard and put the entire profile on the same cholesterol scale. In addition, if the dye is changed to Nile Red, for example, the function can be adjusted for the specific emission response of the different dye. In this way, the analytical data is correlated to the number of lipoprotein particles or to a cholesterol equivalent.

The corrected profile, on a common cholesterol scale, can then be fitted with about twenty Gaussians functions at literature density values for the known lipoprotein subgroups to generate populations and concentrations of each of the subgroups. This separation is necessary to identify the emerging risk factors identified by NCEP. Others have used Gaussians for subgroup determination but only after converting the lipoproteins to raw cholesterol which destroys the lipoproteins. By preserving the lipoproteins, post analysis is possible using other techniques to further analyze them. This will be important in the future where the identification of apolipoproteins will be needed for a more advanced test.

It has been discovered that freezing blood serum or plasma at −70° C. or lower, damages the lipoproteins in unpredictable ways. After careful calibration of the process with carefully analyzed fresh serum using enzymatic methods, standards/calibrators were tested and found to have large discrepancies from the assigned values. Further tests analyzing fresh serum and then freezing the serum at −80° C. showed changes that vary from person to person. The VLDL area is usually greatly reduced (10-50%) in unpredictable ways. It is possible that the freezing creates a crystalline water lattice in the particles that breaks up the particles. The use of the gradient is maybe a cryo preservative that keeps the water in a glass phase rather than crystalline phase. Accordingly, frozen serum is preferably not used for calibration of VLDL; therefore fresh serum that is analyzed using other methods is used to calibrate VLDL. Unfortunately, this means using a secondary standard since fresh serum calibrators are not commercially available. Calibration with serum triglyceride values between 75-125 mg/dL have been found to obey the Friedewald equation and provide a good estimate of VLDL as calculated by TG/5=VLDL. Serum that has triglycerides values greater than 125 mg/dL have a high probability of being cholesterol depleted since cholesterol ester transfer protein (CETP) is likely to replace cholesterol with triglycerides. Conversely, serum with triglyceride values less than 75 mg/dL have a high probability of being cholesterol enriched. Preferably, the calibrators used should be neither highly cholesterol enriched nor highly cholesterol depleted. For this reason, in preferred embodiments, the calibrators used should have triglyceride levels of between 75 mg/dL to 125 mg/dL. Preferably, the calibrator is made with pooled serum from 10 or more donors where triglyceride values are between 75-125 mg/dL. Calibrators having triglyceride values less than 75 mg/dL are considered highly cholesterol enriched and those having triglyceride values greater than 125 mg/dL are considered highly cholesterol depleted. Calibrators are made from the described pooled serum by a reference laboratory analysis that separates lipoprotein groups using ultracentrifugation and determines the cholesterol content as accurately as possible by standards known in this art. The serum should also be analyzed using the method of the present invention to insure that the resulting pooled serum does not have an LDL or HDL bias toward predominately buoyant or dense lipoprotein particles. Using the method of the present invention, the LDL for calibrators should have a mean density value between 1.028-1.032 g/cm² and the HDL should have a mean density between 1.085-1.100 g/cm². Thus, it is preferred that LDL and HDL calibrators used be within these respective ranges. Values below these respective values are predominantly buoyant, while those above the respective ranges are predominantly dense.

Additionally, the method determines the particle number of lipoprotein subgroups. A more meaningful risk factor for cardiovascular disease (CVD) can be determined by determination of subgroup fractions and particle size and/or particle number. Particle size is highly correlated to density with small corresponding to dense particles and large corresponding to buoyant particles. The main groups of lipoproteins include VLDL, LDL and HDL. Subgroups of LDL include IDL (intermediate density lipoprotein), LDL I, LDL II, LDL III, and LDL IV. HDL subgroups include HDL 2b, HDL 2a, and HDL 3 subgroups. Other subgroups according to density, currently defined or undefined, may be quantified with the present method as well.

Lipoprotein particle size and particle number for each subgroup is considered increasingly more important as it relates to risk factor for CVD. The following examples demonstrate the difference between measuring LDL particle numbers and the conventional method of measuring cholesterol as a surrogate for particle number.

Patients A, B, C and D all have directly measured LDL cholesterol of 130 mg/dl and are at moderate risk of CVD due to other factors. For a patient at moderate risk of CVD an LDL value of 130 mg/dl is the highest NCEP recommended value.

Patient A has LDL that contains the average amount of cholesterol by weight of about 50% and the density of the LDL is predominately buoyant. This occurs in about 50% of the population. The particle number test shows a LDL cholesterol equivalent value of 130 mg/dl as expected.

Patient B has high triglycerides causing a condition of cholesterol depleted LDL with the cholesterol content being 40% by weight. This condition occurs at various levels in up to 30% of the population. The test reveals the additional particles of LDL that are needed to carry the 130 mg/dl of cholesterol and gives the cholesterol equivalent result of 160 mg/dl. In this case the patient has a falsely low LDL from the standard direct LDL test and based on the LPP test should be treated according to the NCEP guidelines to reduce LDL.

Patient C is determined from the test to have a Type B LDL profile with 60% of the LDL being small and dense LDL III and IV. This condition occurs both independently and in conjunction with the cholesterol depleted condition in about 30% of the population. In this case the 130 mg/dl of cholesterol is contained in may more small and dense LDL particles than if the particles were large and buoyant. The LPP particle number test shows the LDL cholesterol equivalent value of 160 mg/dl which represents the additional number of LDL particles present. Again the patient has a falsely low LDL value from the direct LDL test but can be properly treated with the LPP result.

Patient D has low triglycerides and IDL and has a condition of cholesterol enriched LDL and HDL. This condition occurs at various levels in up to 20% of the population. The test shows fewer than expected LDL particles to carry the 130 mg/dl and gives a cholesterol equivalent result of 100 mg/dl and a much lower LDL risk than expected from a cholesterol measurement. On the other hand the patient shows an enriched HDL cholesterol number as well and a lower HDL particle number than expected from the cholesterol value potentially putting this patient as risk due to low HDL particle numbers.

The purpose of the test described herein is to identify the National Cholesterol Education Programs (NCEP) lipoprotein emerging risk factors for cardiovascular disease and further to measure the number of lipoprotein particles in each lipoprotein group and subgroup. Lipoprotein groups are VLDL, LDL, and HDL. Subgroups are measured for VLDL, LDL as IDL and LDL I, II, III and IV and for HDL as 2b, 2a and 3. To determine the NCEP emerging risk factors the subgroup values of the lipoproteins need to be determined. The NCEP emerging risk factors are RLP (or remnant lipoprotein), dense LDL, Lp(a) and the subgroup distribution of HDL. RLP, dense LDL and HDL subgroups are directly determined by LPP. Lp(a) is estimated as the value of LDL IV since the Lp(a) density range mostly overlaps the density range of LDL IV. Clinically, high values for LDL IV and Lp(a) have very similar if not identical treatment recommendations. Additionally, assay's for Lp(a) are poor and results vary widely so an approximate value from the LDL IV region is a better estimate of Lp(a) than most assays.

Traditionally a number of approximate methods have been used to measure the NCEP emerging risk factors but generally on a cholesterol basis. The goal of this test is to not only determine all of the emerging risk factors but to present the results in the more clinically relevant particle numbers. The test is the first method to separate the lipoproteins into groups and subgroups and also measure the particles numbers for each of these. The separation method for this test is analytical ultracentrifugation, the CDC gold standard for lipoprotein separation. The lipoprotein particles are stained with a fluorescent dye that saturates the surface of the particles and the measurement of particle numbers is made by measuring the fluorescence.

The test described herein overcomes several historical technology barriers to an optimum lipoprotein test by providing a clear separation of lipoprotein subgroups based on density, a method to calibrate the process using traditional cholesterol standards for all lipoprotein groups and a means to measure lipoprotein particle numbers in each subgroup.

Generally, fasting blood serum is separated from whole blood in a serum separator tube Serum is preferably stored and shipped for up to 5 days at 2-8° C. In a 1.5 mL tube, 6.5 µL of serum is added to 712 µL of gradient material comprising a non-ionic mixture of Nycodenz and Iodixanol with a dilute phosphate buffer and 5 µL of NBD C6-ceramide dye made by dissolving 1 mg of NBD C6-ceramide in 500 µL of (preferably) DMSO. The mixture is vortexed and incubated, preferably at 37° C. for 35 minutes for dye uptake. A mixture of two tri-iodobenzene derivatives is used as a gradient material to get the best possible separation of the most important subgroups of LDL and HDL and keep the separation time reasonable with respect to a work day. Better subgroup separations can be obtained with different gradients or mixtures of the above gradients if longer spin times are used.

As mentioned, DMSO is the preferred solvent in which to dissolve and deliver the fluorescent dye (or other analyte, such as an environment-sensitive chromophore, in cases where an external analyte is required) to the serum sample. Solvents tend to denature (i.e., de-lipidate) lipoproteins. It has been found that DMSO minimizes or eliminates this unwanted effect. It is preferable to limit the contact time of the serum and the solvent as much as possible to minimize any denaturation. This may be accomplished by delivering the dye in DMSO (or other solvent) solution to the cap of a vortex tube. Because of the small volumes delivered, the effects of surface tension keep the solution against the cap. The serum and gradient material are added to the vortex tube itself. Just before vortexing, the cap is attached to the tube and the tube is inverted, causing the serum/gradient to mix with the dye solution. The mixture is then vortexed immediately (or nearly immediately) thereafter) such that the solvent is immediately diluted and any solvent-caused denaturation is accordingly minimized. While this is a preferred method, other methods can be used. Judicious choice of solvent and methods of mixing are preferable used to minimize the denaturing (i.e., de-lipidation) of the lipoprotein in the serum sample.

NBD C6-ceramide is a phospholipid analog and works by embedding the hydrophobic end into the surface of the phospholipid shell of the lipoprotein. When the NBD hydrophobic end is in the hydrophobic environment of the lipoprotein the hydrophilic end fluoresces. Since the surface of the lipoproteins particles are saturated with NBD dye, the fluorescence is a direct measurement of the particle numbers. Free NBD dye does not fluoresce. Other dyes or methods to count particles, known to those of ordinary skill in the art, may be substituted and used in this the procedure of the present invention. For example, BODIPY FL C5-ceramide, BODIPY FL C13-ceramide, BODIPY TR C5-ceramide, and BODIPY FL C12-glucocerebroside are some non-limiting examples.

500 µL of the above solution containing serum, dye and gradient is pipetted into a 0.5 mL centrifuge tube and the tube is spun at 120,000 rpm at 22° C. set point with 22° C. being reached in a Beckman Optima TLX ultracentrifuge or equivalent for 3.0 hours. After the first spin, 90 µL of a dilute phosphate buffer is layered on top of the partially separated mixture and the sample is spun for an additional 30 min at 120,000 rpm at 22° C. set point.

During the first 3.0 hour spin most of the LDL and HDL is separated into subgroups in the continuous gradient formed and the VLDL goes to the lowest density at the top of the tube. The lowest density of the gradient after the spin is approximately 1.020 g/cm$^3$ and at the bottom of the tube the highest density is approximately 1.30 g/cm$^3$. Preferably, the addition of a weak buffer layer for the last 30 min spin forms a diffusion gradient and the buoyant subgroups of LDL and VLDL subgroups migrate to their proper density in the newly formed diffusion gradient (d=1.000 to 1.020) at the top of the tube. At the end of the spin, the tubes are preferably held at room temperature which is approximately 22° C.

The contents of the tubes are preferably extracted using a microfactionator (one non-limiting example is a Brandel FR 115 microfractionator, however, other suitable equivalent devices may be used). The microfractionator is a device that pushes a plunger with a hole in the middle into the centrifuge tube and forces the contents into a micro-cell (i.e., flow cell such as an HPLC flow cell) fluorescence detector. Other flow/injection methods and apparatuses known to those of skill in the art are also applicable and may be substituted. At the end of the extraction the sample in the transfer tube between the fractionator and the detector is pushed into the detector with an HPLC pump and the system is cleaned by purging the tubing with the HPLC pump. The detector software records the fluorescence profile. In alternative embodiments, environment-sensitive chromophores can be used with, or instead of, a fluorophore, and an absorbance detector can be used to measure absorbance, which is then used as the analytical signal. Additionally, other analytical techniques, known to those of ordinary skill in the art may be used. Radioassays using radioactive isotopes are one example. Electrochemical detection of any kind are also alternatives methods of detecting.

Raw data is then preferably corrected for start position and the time scale is converted to a density scale previously determined by collecting small fractions from the microfractionator and accurately measuring the density versus time. The intensity data is preferably then converted to a cholesterol scale by transforming the data by a function, empirically adjusted, but originally derived from the ratio of the surface area of each lipoprotein group or subgroup divided by the volume of the particles, the resulting ratio is multiplied by the cholesterol content for the group or subgroup expressed as a fraction. Specifically, the data is divided by the function. Since the surface of the particles is saturated with dye the SAVR ratio will normalize the fluorescence response for the potential cholesterol volume contained within each particle. Small empirical adjustments may be made to the SAVR function using well known cholesterol standards to account for the differences in the phospholipid shell of each lipoprotein type and the dye uptake.

The ratio of surface area to (volume multiplied by cholesterol content expressed as a fraction) used as a correction gives accurate results as per lipoprotein particle profiles to a first approximation. Other correction factors may also be used to improve the normalization of the analytical data. Such corrections may include those accounting for difference in lipoprotein phospholipid surface concentrations of the various lipoprotein groups and subgroups and for the cholesterol content of the various lipoprotein groups and subgroups. If these and other proper normalization functions can be ascertained, they should improve the accuracy of results. Additionally, small empirical corrections are made to account for lipoprotein phospholipids surface variation. However, all of these adjustments are of minor significance in comparison to the SAVR correction. The SAVR corrected data, now on a cholesterol scale is integrated after fitting the data with an appropriate function, such as Gaussian function.

Preferably, twenty Gaussian peaks are defined, with one to three peaks per lipoprotein subgroup, at the specific densities as defined by a general consensus, from the literature, for the lipoprotein subgroups density ranges. The width and density or position of each Gaussian peak is held mathematically constant or allowed to change only slightly and the magnitude of the Gaussian is allowed to vary in a least squares regression to fit the measured data. The integration of the area of the Gaussian peaks determines the unscaled magnitude, in cholesterol units, of each lipoprotein subgroup.

A scale factor is applied to the resulting integration values so that for the "normal" person that is not cholesterol depleted or enriched, a value for an independent cholesterol standard matches the value obtained for the LPP test LDL and HDL result. In cases where triglycerides are over 125 mg/dL, the patient is often lipoprotein cholesterol depleted and when the triglyceride (TG) value is under 75 mg/dL, the patient is often lipoprotein cholesterol enriched. To find a standard where the VLDL values approximately fits the Friedewald formula, with TG/5=VLDL, the TG value needs to be between 75 and 125 mg/dL. Using several specimens with values in this range, suitable VLDL standards can be found to calibrate the VLDL section of the profile. Freezing the standards also changes the VLDL and IDL regions of the profile due to break up of the particles so unfrozen serum is best for this calibration.

Since the SAVR function covers the entire lipoprotein subgroup range from VLDL through HDL, the calibration above based only on the three points from VLDL, LDL and HDL is preferably extended to all lipoprotein subgroups where cholesterol or particle number standards due not exist and this overcomes the traditional barrier to determining these values.

Since the actual fluorescence response is due to the number of particles rather than cholesterol content, the values obtained as "cholesterol equivalent of lipoprotein particle numbers" are only equal to a cholesterol assay for the average person with the average percent of cholesterol per lipoprotein particle. Values that are higher than expected from a cholesterol assay indicate cholesterol depleted lipoproteins and more particles than expected. Values that are lower than expected from a cholesterol assay indicate cholesterol enriched lipoproteins and fewer particles than expected. Approximately 25-30% of the population is LDL cholesterol depleted (usually when high triglycerides are present the cholesterol ester transfer protein (CETP) transfers triglycerides to LDL and displaces cholesterol) putting this group at greater risk of cardiovascular disease than expected from an LDL cholesterol test. Approximately 15-20% of the population is LDL cholesterol enriched giving a lower LDL risk level than expected. This has been observed when VLDL and IDL regions of the profile are low. The actual mechanism is not known. The opposite risk relationship occurs for HDL in these two examples. When HDL is cholesterol enriched the values from a standard cholesterol test may predict more particles than actually exist and underestimate the true risk.

The calculation that generates particle numbers in nmol/L from the experimentally determined "equivalent" cholesterol values uses the average published cholesterol content of the particles, the published size or volume, and the experimentally determined density. In this way the particle numbers for all lipoprotein groups and subgroups are determined.

The cholesterol equivalent calculation for "total cholesterol" is the sum all of the components of the profile, namely VLDL, LDL and HDL. In this way, the total cholesterol value always equals the sum of the parts which rarely occurs in separate assays for triglycerides or LDL and HDL cholesterol. A mathematical mean density value is calculated for LDL and HDL as a group indication of LDL phenotype type A, I or B and buoyant or dense HDL designation. FIG. 1 illustrates a healthy lipid number profile in (a); and an atherogenic profile in (b).

A new algorithm to calculate fractional metabolic syndrome traits has been developed. For example, if HDL is greater than 40 mg/dL but less than 50 mg/dL, with <40 mg/dL giving one trait, (i.e. if HDL=42 mg/dL then 0.8 traits are calculated rather than zero) fractional values are determined. The same is true for triglycerides using the equivalent VLDL value. The density of LDL also generates up to one trait following the lead of NCEP and the connection of dense LDL to metabolic syndrome. In this way, up to three traits can be calculated giving a diagnosis of metabolic syndrome from lipoprotein traits alone. Additionally, since the traits are calculated from the particle number data rather than cholesterol this important difference is taken into account. An exponential function is used to calculate the fractional metabolic syndrome traits so, for example, zero traits are calculated for an HDL=50 and 0.5 traits for HDL=45. If a person had a triglyceride value of 140 mg/dL, an HDL value of 42 mg/dL and a very dense LDL profile, the standard calculation would give zero metabolic syndrome traits and a miss diagnosis of metabolic syndrome. In this example, even for a standard cholesterol assay, the experimental error is within the threshold values. In the LPP fractional trait calculation, the above calculation gives 2.8 traits and a probable diagnosis of metabolic syndrome. A diagnosis of metabolic syndrome raises an individual's cardiovascular risk one level and is an indication of insulin resistance.

A generalized schematic example of the calculation of lipoprotein particle numbers from fluorescence data is shown below. The data in each case is shown as a data array:

LPP Data Processing Flow Diagram:

| | | |
|---|---|---|
| 1. | Raw Data (E.g., Fluorescence) Points of Profile | $X_1, X_2, X_3, \ldots X_n$ |
| 2. | Divide data points by SAVR function which is the [Surface Area of the Lipoprotein/(Volume of the Lipoprotein × Cholesterol content)]; Converts Date to a Cholesterol Scale | $X_{1h}, X_{2h}, X_{3h}, \ldots X_{nh}$ |
| 3. | Integrate the $X_{nh}$ data (previously fitted with an appropriate function such as a Gaussian function) at Defined Lipoprotein Subgroup Densities To Determine Subgroup Values on a Cholesterol Scale | $X_{1i}, X_{2i}, X_{3i}, \ldots X_{ni}$ |
| 4. | Scale $X_{1i}$ Data to using known Cholesterol Standards that preferably are Neither Cholesterol Depleted nor Enriched; Neither Buoyant nor Dense | $X_{1j}, X_{2j}, X_{3j}, \ldots X_{nj}$ |
| 5. | Use $X_{1j}$ Data to Calculate Lipoprotein Particle Numbers | $Y_1, Y_2, Y_3, \ldots Y_n$ |

An example of a lipoprotein particle calculation from scaled, fitted and integrated data is provided below. An arbitrary value of 100 mg/dl for the scaled data ($X_{nj}$) is used in the example below to arrive at a lipoprotein particle number ($Y_n$).

Calculation for 100 mg/dl as a cholesterol equivalent of each lipoprotein subgroup:

| Lipoprotein | Size nm | % cholesterol | Density g/cm$^3$ | Particle Number nmol/L |
|---|---|---|---|---|
| IDL | 25 | 45 | 1.012 | 446 |
| LDL 1 | 22 | 52 | 1.021 | 561 |
| LDL II | 20.5 | 54 | 1.029 | 663 |
| LDL III | 19 | 47 | 1.039 | 947 |
| LDL IV | 18 | 42 | 1.047 | 1237 |

Assumptions: LDL II particle 20.5 nm in diameter, 10.25 nm radius, LDL cholesterol equivalent value of 100 mg/dl and an LDL II density of 1.029. An LDL II particle is 54% cholesterol.

1. 10.25 nm particle gives a volume $(4/3\pi r^3) =$ $$4510 \text{ nm}^3 \text{ or } 4.510 \times 10^3 \text{ nm}^3$$

2. 100 mg/dl = 1.00 g/liter cholesterol equivalent concentration 3. 1.029 g/cm$^3$ density converted to g/nm$^3$ = $1.029 \times 10^{-3}$ g/mm$^3$ $$= 1.029 \times 10^{-12} \text{ g/}\mu\text{m}^3$$

$$= 1.029 \times^{-21} \text{ g/nm}^3$$

4. Calculate the weight of a particle $4.510 \times 10^3$ nm$^3$ (column)$\times 1.029 \times 10^{-21}$ g/nm$^3$ (density)=$4.641 \times 10^{-18}$ g 5. Calculate the weight of cholesterol in a particle $4.641 \times 10^{-18}$ g$\times 54\% = 2.506 \times 10^{-18}$ g cholesterol 6. Calculate lipoprotein particle number per liter $$\frac{1.000 \text{ g/liter (cholesterol concentration)}}{2.506 \times 10^{-18} \text{ g of cholesterol/particle}} = 0.3990 \times 10^{18} \text{ particles/liter}$$

7. Treating particles like molecules, we calculate moles of particles $$\frac{0.3990 \times 10^{18} \text{ particles/liter}}{6.0225 \times 10^{23} \text{ particles/mole}} = 0.0663 \times 10^{-5} \text{ moles/liter or,}$$

$663 \times 10^{-9}$ mol/L or, 663 nmol/L

Although the present invention and its advantages have been described in detail, it should be understood that various changes, substitutions and alterations can be made herein without departing from the spirit and scope of the invention as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure of the present invention, processes, machines, manufacture, compositions of matter, means, methods, or steps, presently existing or later to be developed that perform substantially the same function or achieve substantially the same result as the corresponding embodiments described herein may be utilized according to the present invention. Accordingly, the appended claims are intended to include within their scope such processes, machines, manufacture, compositions of matter, means, methods, or steps.

What is claimed is:

1. A method of evaluating the lipoprotein profile of a non-human animal or human, said method comprising:
   (a) obtaining a blood sample of said non-human animal or human;
   (b) separating serum from said blood sample;
   (c) delivering the serum to a centrifuge tube and adding an analyte material and a self generating gradient material to form a mixture;
   (d) centrifuging some or all of the mixture;
   (e) extracting the centrifuged mixture to form an extracted mixture;
   (f) measuring an analytical signal from the extracted material;
   (g) recording data comprising said analytical signal;
   (h) converting said data to cholesterol equivalent data, said step of converting comprising the step of transforming the data with a SAVR function (surface area to volume ratio weighted by cholesterol content expressed as a fraction) for each lipoprotein group and/or subgroup, wherein said data is normalized with said function for the potential cholesterol content contained within each particle;
   (i) transforming said cholesterol equivalent data using a calibration process with data from lipoprotein cholesterol standards; and,
   (j) thereafter calculating particle number data from said transformed cholesterol equivalent data.

2. The method of claim 1, wherein said step of transforming said cholesterol equivalent data using a calibration process with data from lipoprotein cholesterol standards comprises the use of data from lipoprotein cholesterol standards that neither have a high probability of being cholesterol enriched nor have a high probability of being cholesterol depleted; and, that are neither predominantly buoyant nor predominantly dense.

3. The method of claim 1, wherein said step of measuring an analytical signal comprises passing the extracted mixture through a flow cell.

4. The method of claim 1, further comprising the step of incubating at an elevated temperature after step (c).

5. The method of claim 4, wherein said step of incubation at an elevated temperature comprises incubating at 23-50° C.

6. The method of claim 4, wherein said step of incubating further comprises vortexing the mixture.

7. The method of claim 1, wherein said step of adding a self generating gradient material comprises delivering a composition comprising a compound selected from the group consisting of Nycodenz, Iodixanol, and any combination thereof.

8. The method of claim 1, wherein said step of adding an analyte material comprises adding a fluorescent dye.

9. The method of claim 8, wherein said step of measuring an analytical signal comprises measuring fluorescence.

10. The method of claim 8, wherein said step of adding a fluorescent dye comprises adding NBD C6-ceramide dye.

11. The method of claim 1, wherein said step of adding an analyte material comprises adding an environment-sensitive chromophore.

12. The method of claim 11, wherein said step of measuring an analytical signal comprises measuring absorbance.

13. The method of claim 1, wherein said step of adding an analyte material comprises adding a radio isotope.

14. The method of claim 13, wherein said step of measuring an analytical signal comprises measuring radiation emitted by said radio isotope.

15. The method of claim 1, wherein said step of centrifuging comprises centrifuging at about 120,000 rpm and about 7° C. for about 4.0 hours.

16. The method of claim 15, further comprising the step of adding a dilute phosphate buffer and centrifuging for about 30 minutes at about 120,000 rpm at about 7° C., said step of adding dilute phosphate buffer and centrifuging for about 30 minutes being performed after said step of centrifuging at about 120,000 rpm and about 7° C. for about 4.0 hours.

17. The method of claim 16, wherein said step of adding a dilute phosphate buffer comprises adding about 10-300 μL of said dilute phosphate buffer.

18. The method of claim 1, wherein said step of centrifuging comprises centrifuging at about 120,000 rpm and about 22° C. for about 3.0 hours.

19. The method of claim 18, further comprising the step of adding a dilute phosphate buffer and centrifuging for about 30 minutes at about 120,000 rpm at about 22° C., said step of adding dilute phosphate buffer and centrifuging for about 30 minutes being performed after said step of centrifuging at about 120,000 rpm and about 22° C. for about 3.0 hours.

20. The method of claim 1, wherein said step of extracting comprises separating fractions of different densities of said mixture.

21. The method of claim 1, wherein said step of passing the extracted mixture through a flow cell comprises pumping said extracted mixture with an HPLC pump.

22. The method of claim 1, further comprising the step of correcting said data for start position and using a time scale converted to a density scale, said density scale determined by collecting fractions from said step of extracting.

23. The method of claim 1, wherein said step of converting said data to cholesterol equivalent data further comprises the step of making small empirical adjustments to said function using known cholesterol standards to account for the differences in the phospholipids shell of each lipoprotein type and dye uptake.

24. The method of claim 1, wherein said step of correlating comprises calculating a lipoprotein particle number or a cholesterol equivalent value from said data.

25. The method of claim 1, wherein said step of delivering the serum to a centrifuge tube comprises delivering about 1-30 μL to said centrifuge tube.

26. The method of claim 1, wherein said step of adding an analyte material and a self generating gradient material comprises adding about 100-1500 μL of said self generating gradient material.

27. The method of claim 1, wherein said step of adding an analyte material comprises adding about 1-30 μL of a dye solution.

28. The method of claim 1, wherein said step of delivering the serum to a centrifuge tube and adding an analyte material and a self generating gradient material to form a mixture comprises delivering a total volume of 100-1200 μL.

* * * * *